US012714328B2

(12) United States Patent
Greene et al.

(10) Patent No.: US 12,714,328 B2
(45) **Date of Patent: *Aug. 25, 2026**

(54) METHODS FOR LOCALIZING MARKERS WITHIN A BODY

(71) Applicant: Cianna Medical, Inc., Aliso Viejo, CA (US)

(72) Inventors: John E. Greene, Valley Center, CA (US); Jonathan Edward White, Aliso Viejo, CA (US); Kohl Ian Thorlakson, Aliso Viejo, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/805,335

(22) Filed: Aug. 14, 2024

(65) Prior Publication Data

US 2025/0090042 A1 Mar. 20, 2025

Related U.S. Application Data

(63) Continuation of application No. 16/917,570, filed on Jun. 30, 2020, now Pat. No. 12,082,919.

(Continued)

(51) Int. Cl.
*A61B 5/06* (2006.01)
*A61B 5/00* (2006.01)

(52) U.S. Cl.
CPC ............ *A61B 5/064* (2013.01); *A61B 5/0031* (2013.01); *A61B 5/4312* (2013.01); *A61B 2562/182* (2013.01)

(58) Field of Classification Search
CPC .... A61B 2034/2051; A61B 2090/3908; A61B 2090/3925; A61B 2090/3966;

(Continued)

(56) References Cited

U.S. PATENT DOCUMENTS 6,061,589 A * 5/2000 Bridges ................ A61B 6/0435 600/430
6,918,919 B2 7/2005 Krag (Continued)

FOREIGN PATENT DOCUMENTS

CN 101437455 A 5/2009
CN 101437455 B 3/2013

(Continued)

OTHER PUBLICATIONS

"Different Types of Antennas & Characteristics of Antenna," Mar. 4, 2019, Electronics Hub (Year: 2019).*

(Continued)

*Primary Examiner* — Michael J Carey
*Assistant Examiner* — Maria Christina Talty
(74) *Attorney, Agent, or Firm* — Dorsey & Whitney LLP

(57) ABSTRACT

Probes and related systems and methods are provided for localizing markers implanted within a patient's body. The probe includes an antenna assembly adjacent a distal end thereof including a ceramic base including a planar distal surface and four proximal surfaces extending at an angle relative to a longitudinal axis of the probe to define a generally pyramidal shape. The base includes antenna elements on the proximal surfaces and radial slots between adjacent proximal surfaces to substantially isolate the antenna elements from one another. A controller is coupled to the antenna elements for transmitting signals into a patient's body and receiving reflected signals reflected from a marker implanted within the patient's body to identify and/or localize the marker.

18 Claims, 8 Drawing Sheets

Related U.S. Application Data

(60) Provisional application No. 62/871,059, filed on Jul. 5, 2019.

(58) Field of Classification Search
CPC ...... A61B 2090/397; A61B 2090/3975; A61B 2562/182; A61B 5/0031; A61B 5/064; A61B 5/4312; A61B 90/04; A61B 90/39; A61B 90/98; H01L 2223/6677; H01L 23/60; H01L 23/66
See application file for complete search history.

(56) References Cited

U.S. PATENT DOCUMENTS

| | | | | |
|---|---|---|---|---|
| 9,155,473 | B2 | 10/2015 | Kang | |
| 2002/0065512 | A1 | 5/2002 | Fjield et al. | |
| 2003/0036713 | A1* | 2/2003 | Bouton | A61B 5/411 600/587 |
| 2005/0151650 | A1 | 7/2005 | Wright et al. | |
| 2011/0313288 | A1* | 12/2011 | Chi Sing | A61B 8/0825 600/437 |
| 2013/0345553 | A1 | 12/2013 | Arts et al. | |
| 2014/0276031 | A1* | 9/2014 | Lomnitz | A61B 5/4312 600/430 |
| 2016/0354177 | A1* | 12/2016 | Rulkov | A61B 90/37 |
| 2017/0143398 | A1 | 5/2017 | Young et al. | |
| 2017/0296289 | A1 | 10/2017 | Andrews et al. | |
| 2017/0296298 | A1 | 10/2017 | Sillers | |
| 2018/0261566 | A1 | 9/2018 | Babcock et al. | |
| 2018/0279907 | A1 | 10/2018 | Greene et al. | |
| 2021/0000382 | A1 | 1/2021 | Greene et al. | |

FOREIGN PATENT DOCUMENTS

| | | | |
|---|---|---|---|
| CN | 104515807 | A | 4/2015 |
| CN | 104806216 | A | 7/2015 |
| CN | 105007815 | A | 10/2015 |
| CN | 106413524 | A | 2/2017 |
| CN | 108474837 | A | 8/2018 |
| WO | 2014149183 | | 9/2014 |
| WO | 2017205978 | A1 | 12/2017 |

OTHER PUBLICATIONS

Bahramiabarghouei , et al., “Flexible 16 Antenna Array for Microwave Breast Cancer Detection”, IEEE Transaction on Biomedical Engineering, vol. 62 Ni. 10, Oct. 2015, 10 pgs.

Malyhe , et al., “Ultra Wideband Compact Near-Field Imaging System for Breast Cancer Detection”, IET Microw, Antennas Propag., vol. 9 Issue 10, 2015, 1009-1014.

International Search Report and Written Opinion dated Oct. 15, 2020 for PCT/US2020/040353.

Notice of Allowance dated May 22, 2024 for U.S. Appl. No. 16/917,570.

Office Action dated Feb. 23, 2023 for U.S. Appl. No. 16/917,570.

Office Action dated Aug. 25, 2022 for U.S. Appl. No. 16/917,570.

Office Action dated Oct. 26, 2023 for U.S. Appl. No. 16/917,570.

“Different Types of Antennas ND Characteristics of Antenna”, http://www.electronicshub.org, Mar. 14, 2019.

Joshi , et al., “Compact Dual Band Convexo-Concave Microstrip Patch Antenna Having Bow Tie Slot with Alteration of Dielectric Substrate for Remote Sensing Applications”, IEEE International Conference on Recent Advances and Innovations in Engineering, Jaipur India, Dec. 23-25, 2016.

Bahramiabarghouei, et al., “Flexible 16 Antenna Array for Microwave Breast Cancer Detection”, IEEE Transaction on Biomedical Engineering, vol. 62 No. 10, Oct. 2015, 2516-2525.

* cited by examiner 40
42
44
44a
44b
45
48
54
50
52

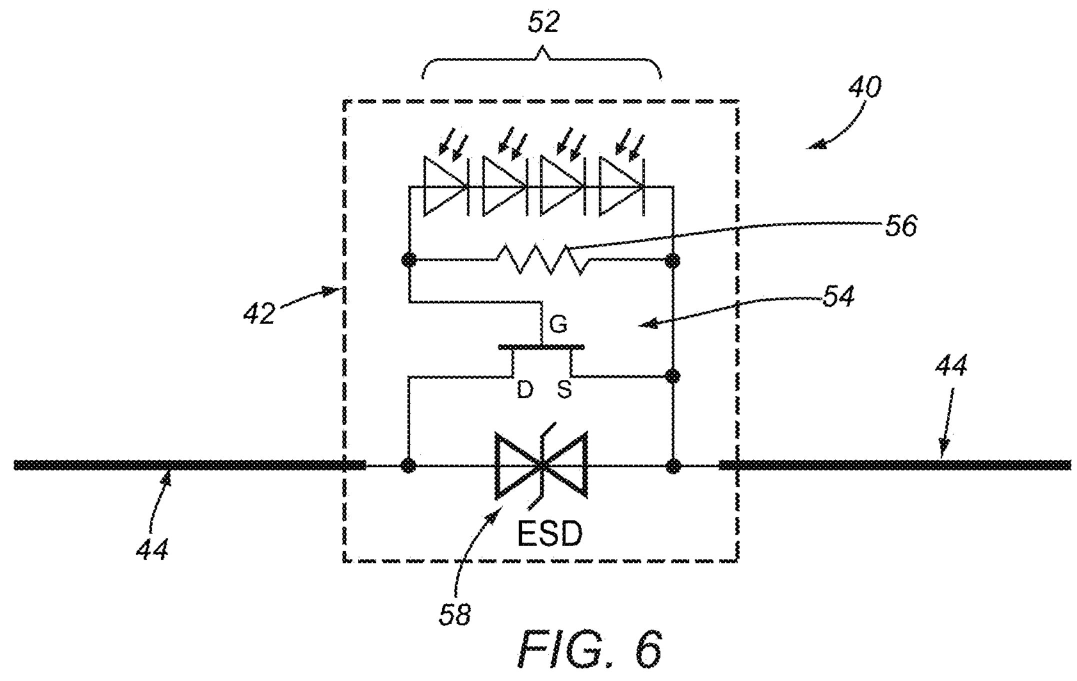
FIG. 6
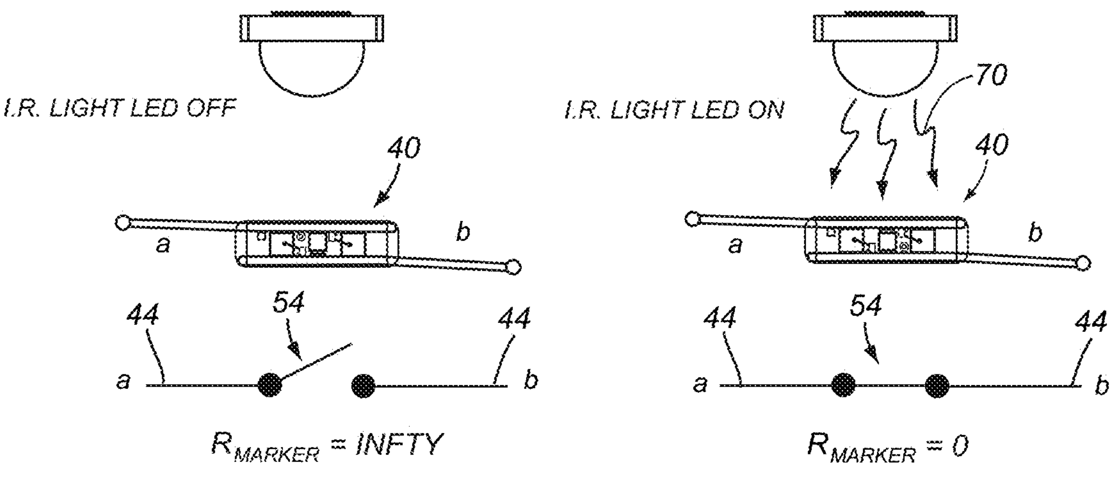
FIG. 7A
FIG. 7B

METHODS FOR LOCALIZING MARKERS WITHIN A BODY

RELATED APPLICATIONS

This application is a continuation of U.S. patent application Ser. No. 16/917,570, filed Jun. 30, 2020 and titled SYSTEMS AND METHODS FOR LOCALIZING MARKERS WITHIN A BODY, which claims priority to U.S. Provisional Application No. 62/871,059, filed on Jul. 5, 2019 and titled, SYSTEMS AND METHODS FOR LOCALIZING MARKERS WITHIN A BODY, both of which are hereby incorporated by reference in their entireties.

TECHNICAL FIELD

The present disclosure relates to systems and methods for identifying and/or locating markers, including markers implanted within a patient's body, e.g., during surgical procedures or other procedures, such as during lumpectomy procedures.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 6 is an exemplary embodiment of a schematic of a circuit that may be included in the marker of FIGS. 5A and 5B.

FIGS. 7A and 7B are schematics demonstrating operation of a switch of the circuit of FIG. 6.

DETAILED DESCRIPTION

Figure 1:
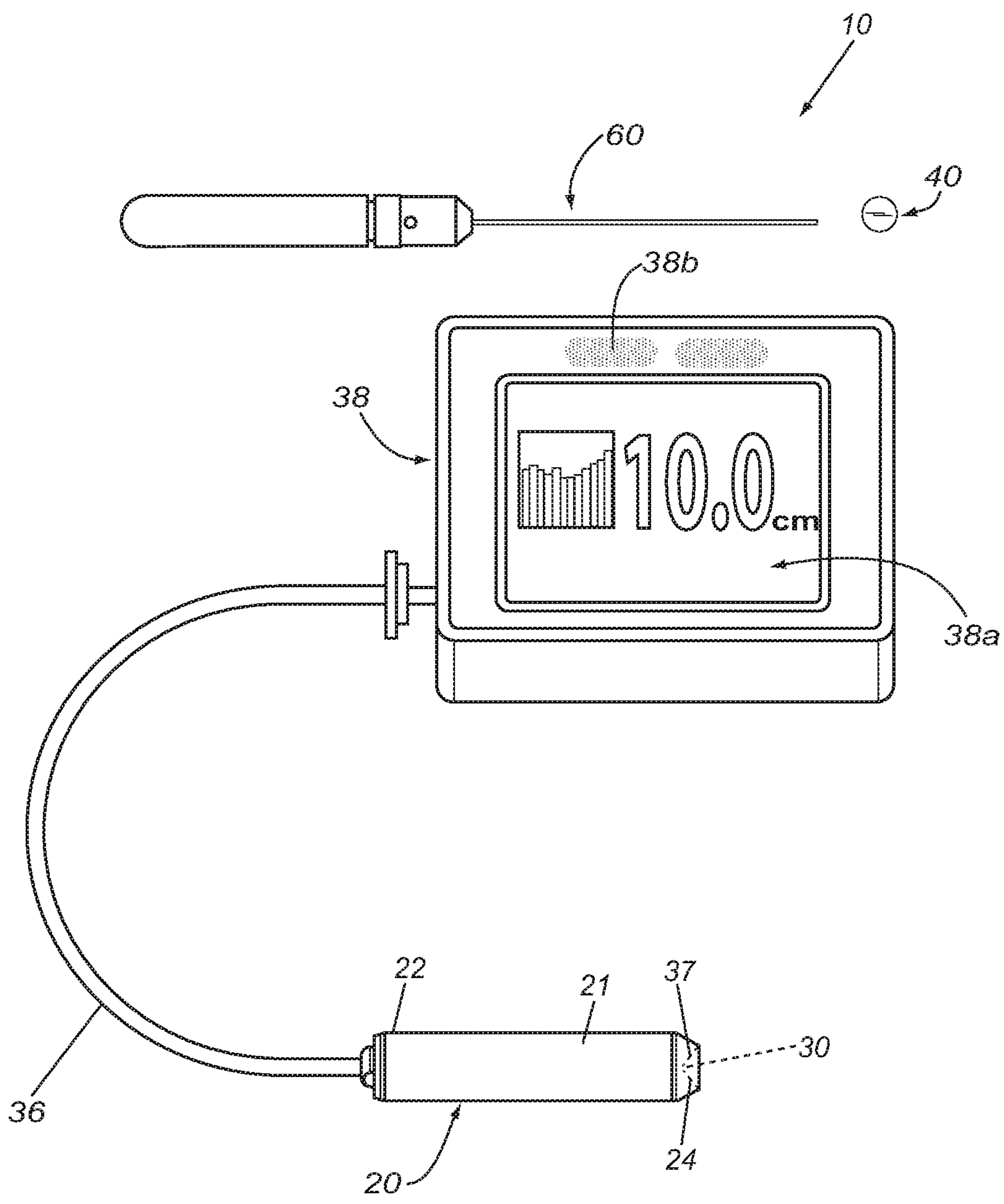
FIG. 1 shows an exemplary embodiment of a system for delivering and localizing a marker within a patient's body including a probe and a delivery device for implanting one or more markers within a patient's body.

Before a biopsy or surgical procedure to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, the surgeon may merely estimate the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Because the seed is delivered through a needle that is immediately removed, there is risk that the seed may migrate within the patient's body between the time of placement and the surgical procedure. Thus, similar to using a localization wire, the seed may not accurately identify the location of the lesion, particularly, since there is no external way to stabilize the seed once placed. Further, such gamma probes may not provide desired precision in identifying the location of the seed, e.g., in three dimensions, and therefore may only provide limited guidance in localizing a lesion.

Accordingly, apparatus and methods for localization of lesions or other tissue structures in advance of and/or during surgical, diagnostic, or other medical procedures would be useful.

The present disclosure is directed to systems and methods for identifying and/or locating markers implanted within a patient's body, e.g., during surgical procedures or other procedures, such as during lumpectomy procedures.

In accordance with one embodiment, a probe is provided for localizing a marker within a patient's body that includes a first member or housing comprising a proximal end, a distal end configured for placement adjacent a patient's body, and a longitudinal axis extending therebetween; an antenna assembly adjacent the distal end comprising a base including a planar distal surface extending substantially perpendicular to the longitudinal axis, and a plurality of proximal surfaces extending at an angle relative to the longitudinal axis, each proximal surface including an antenna element to provide a plurality of antenna elements;

and a controller coupled to the antenna elements for transmitting transmit signals into a patient's body and receiving reflected signals reflected from a marker within the patient's body to identify or localize the marker.

In accordance with another embodiment, a probe is provided for localizing a marker within a patient's body that includes a first member or housing comprising a proximal end, a distal end configured for placement adjacent a patient's body, and a longitudinal axis extending therebetween; an antenna assembly adjacent the distal end comprising a base including a planar distal surface extending substantially perpendicular to the longitudinal axis, four proximal surfaces extending at an angle relative to the longitudinal axis to define a generally pyramidal shape, antenna elements on the proximal surfaces, and radial slots between adjacent proximal surfaces to substantially isolate the antenna elements from one another; and a controller coupled to the antenna elements for causing one or more of the antenna elements to transmit signals into a patient's body and for receiving reflected signals reflected from a marker implanted within a patient's body via one or more of the antenna elements, the controller processing the reflected signals to identify or localize the marker.

In accordance with still another embodiment, a system is provided for identifying and localizing a marker within a patient's body that includes a delivery device for delivering a marker into a patient's body; an antenna probe comprising a proximal end, a distal end configured for placement adjacent a patient's body, and a longitudinal axis extending therebetween, and an antenna assembly adjacent the distal end comprising a base including a planar distal surface extending substantially perpendicular to the longitudinal axis, and a plurality of proximal surfaces extending at an angle relative to the longitudinal axis, each proximal surface including an antenna element to provide a plurality of antenna elements; and a controller coupled to the antenna elements for transmitting transmit signals into a patient's body and receiving reflected signals reflected from a marker within the patient's body to identify or localize the marker.

In accordance with still another embodiment, a method is provided for localizing a marker within a body that includes placing a distal end of a probe against tissue, the probe comprising an antenna assembly adjacent the distal end comprising a base including a planar distal surface placed adjacent the tissue, and a plurality of proximal surfaces extending at an angle relative to a longitudinal axis of the probe; transmitting, by one or more transmit antenna elements on one or more of the proximal surfaces, transmit signals into the body; receiving, by one or more receive antenna elements on one or more of the proximal surfaces, receive signals that are reflected from the marker; and identifying the marker based at least in part on the receive signals.

Other aspects and features of the present disclosure will become apparent from consideration of the following description taken in conjunction with the accompanying drawings.

In the following description, numerous details are set forth in order to provide a more thorough description of the system. It will be apparent, however, to one skilled in the art having the benefit of this disclosure, that the disclosed system may be practiced without these specific details. In the other instances, well known features have not been described in detail so as not to unnecessarily obscure the system.

Figure 2:
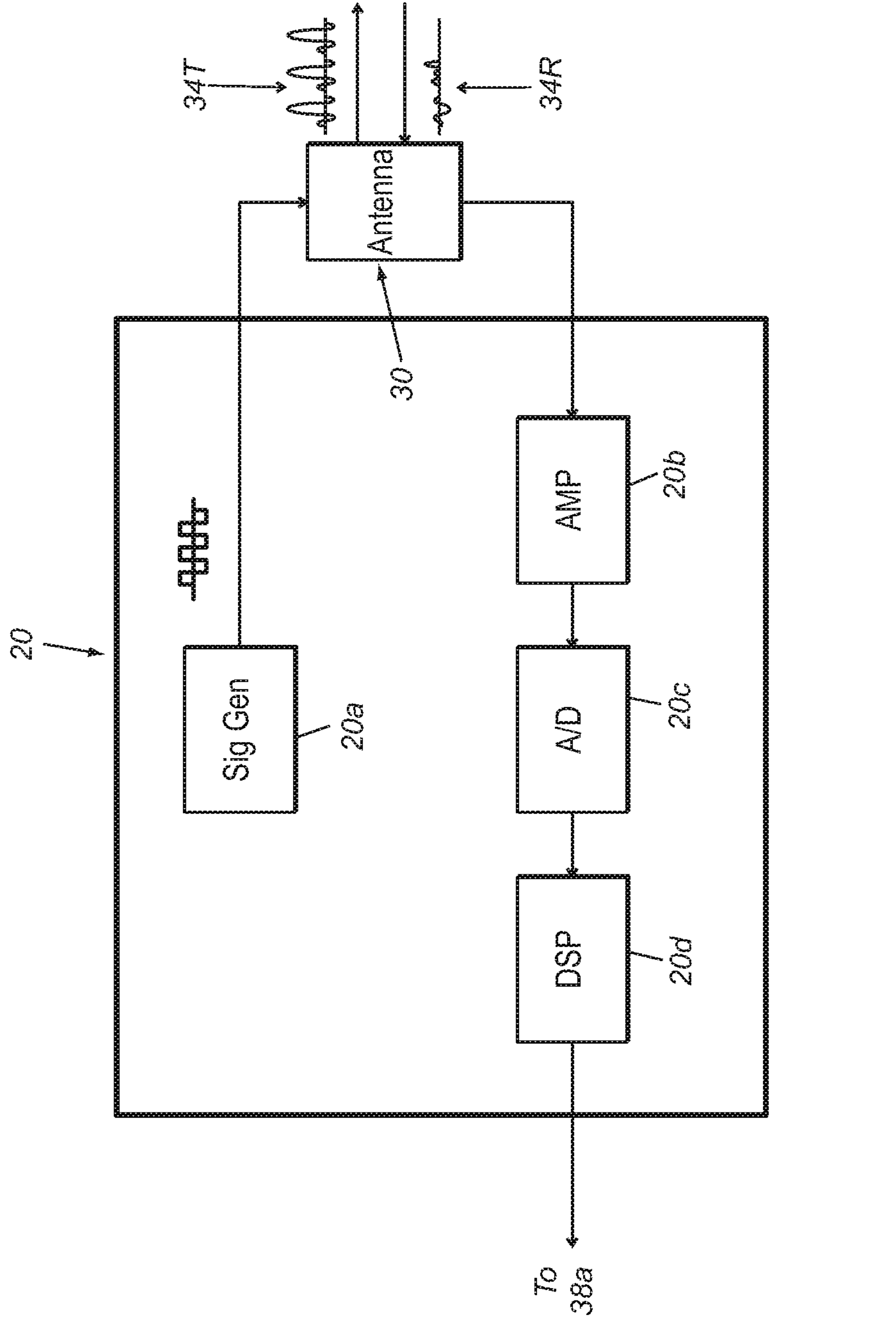
FIG. 2 is block diagram depicting exemplary components of the probe of FIG. 1.
Figures 3A, 3B:
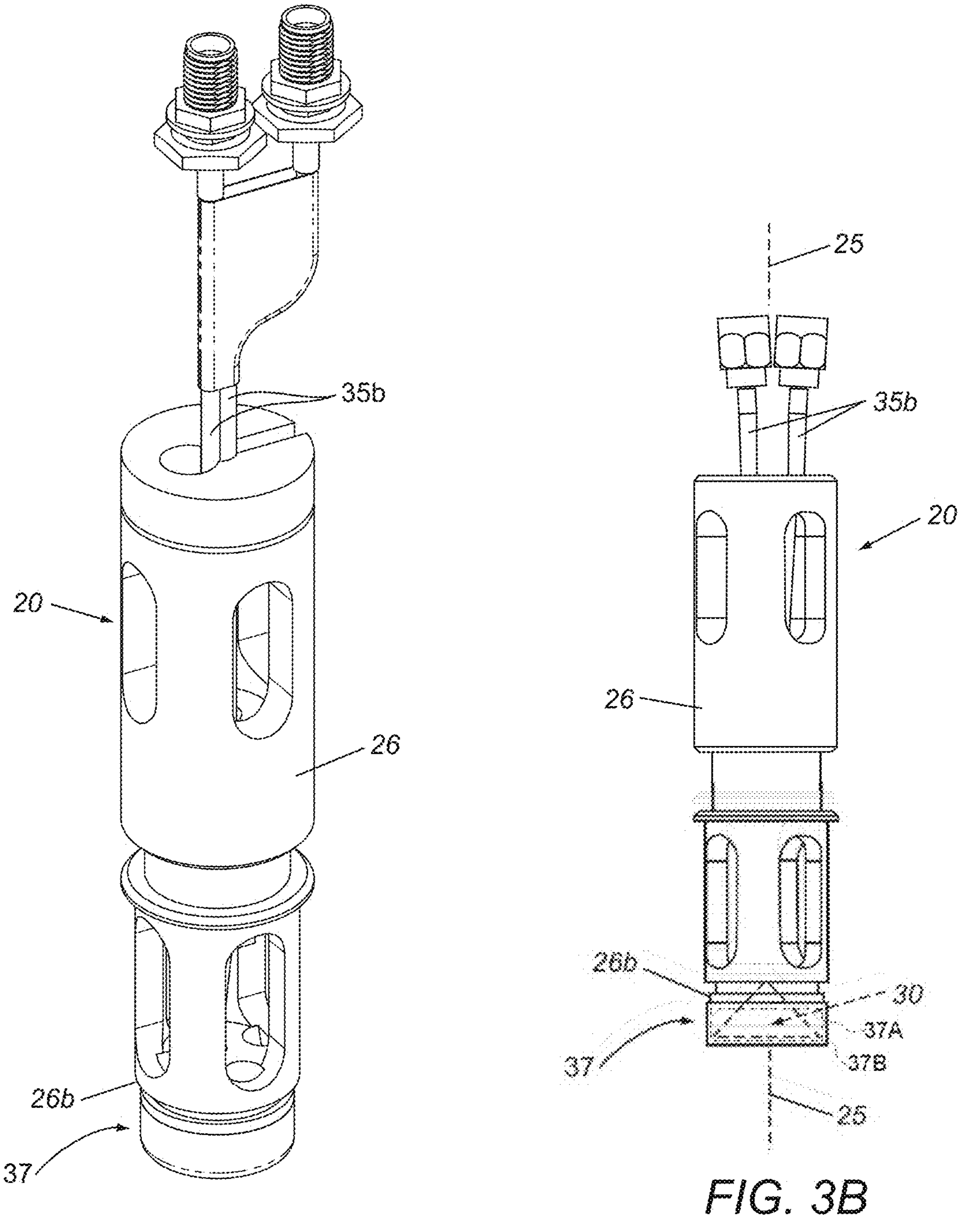
FIGS. 3A-3C are perspective, side, and end views, respectively, of an exemplary probe that may be included in a system such that shown in FIGS. 1-2.
Figures 3C, 9:
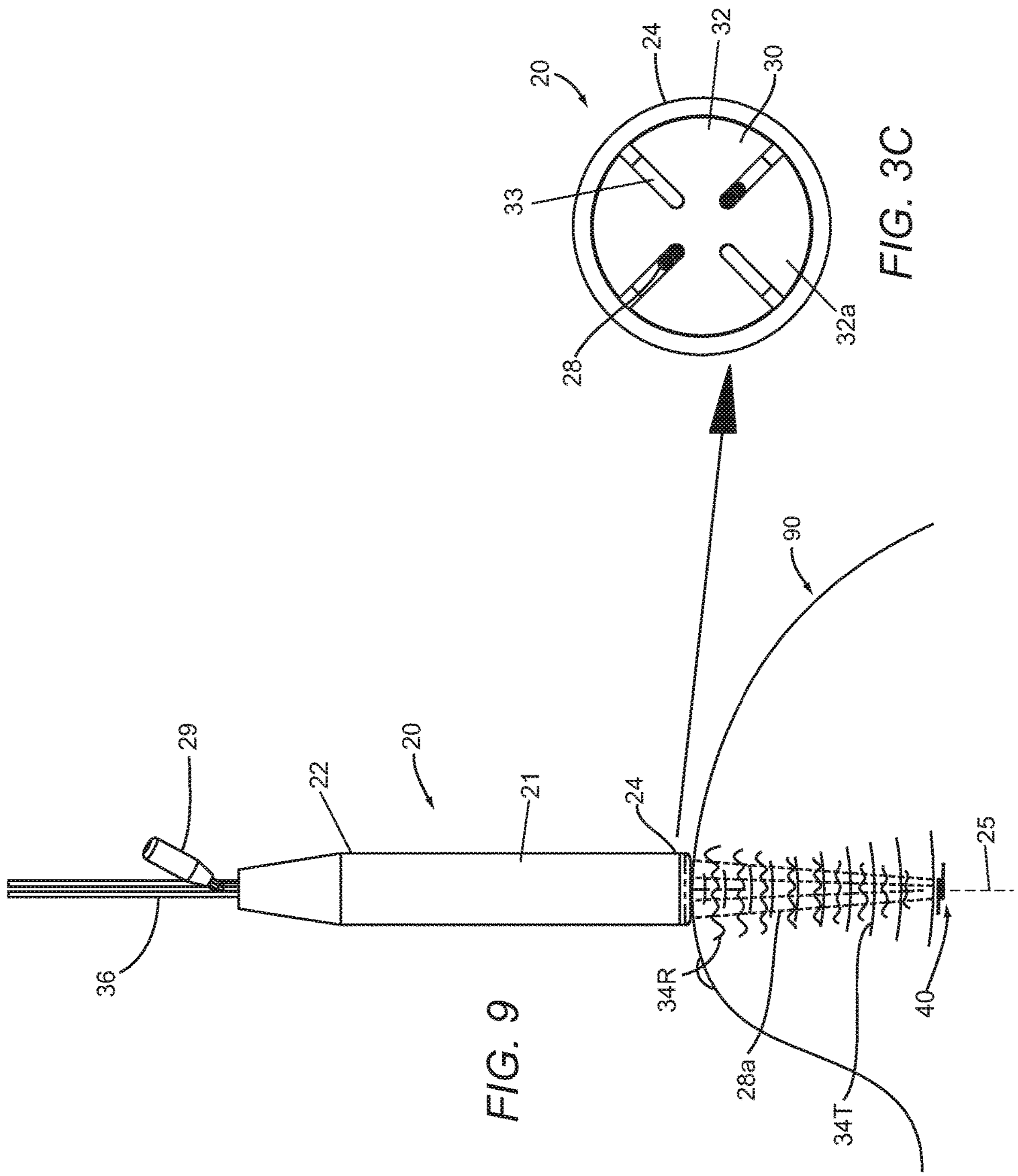
FIG. 9 is a side view of an exemplary embodiment of a probe localizing a marker implanted within a breast.

Turning to the drawings, FIGS. 1-4C show an exemplary embodiment of a system 10 for localization of a target tissue region within a patient's body, e.g., for identifying and/or locating one or more markers implanted within or adjacent a target tissue region, such as a tumor, lesion, or other tissue structure, e.g., a marker 40 implanted within a breast 90 as shown in FIG. 9. As shown in FIG. 1, the system 10 may include a delivery device 60 carrying one or more targets, tags, or markers (one marker 40 shown), a probe 20 for detecting and/or locating the marker 40, e.g., using ultra-wideband radar, and a controller and/or display unit 38 coupled to the probe 20, e.g., using one or more cables 36, generally similar to embodiments described in U.S. Publication Nos. 2011/0021888, 2014/0309522, 2016/0354177, and 2017/0319102, the entire disclosures of which are expressly incorporated by reference herein.

Figures 4A, 4B, 4C:
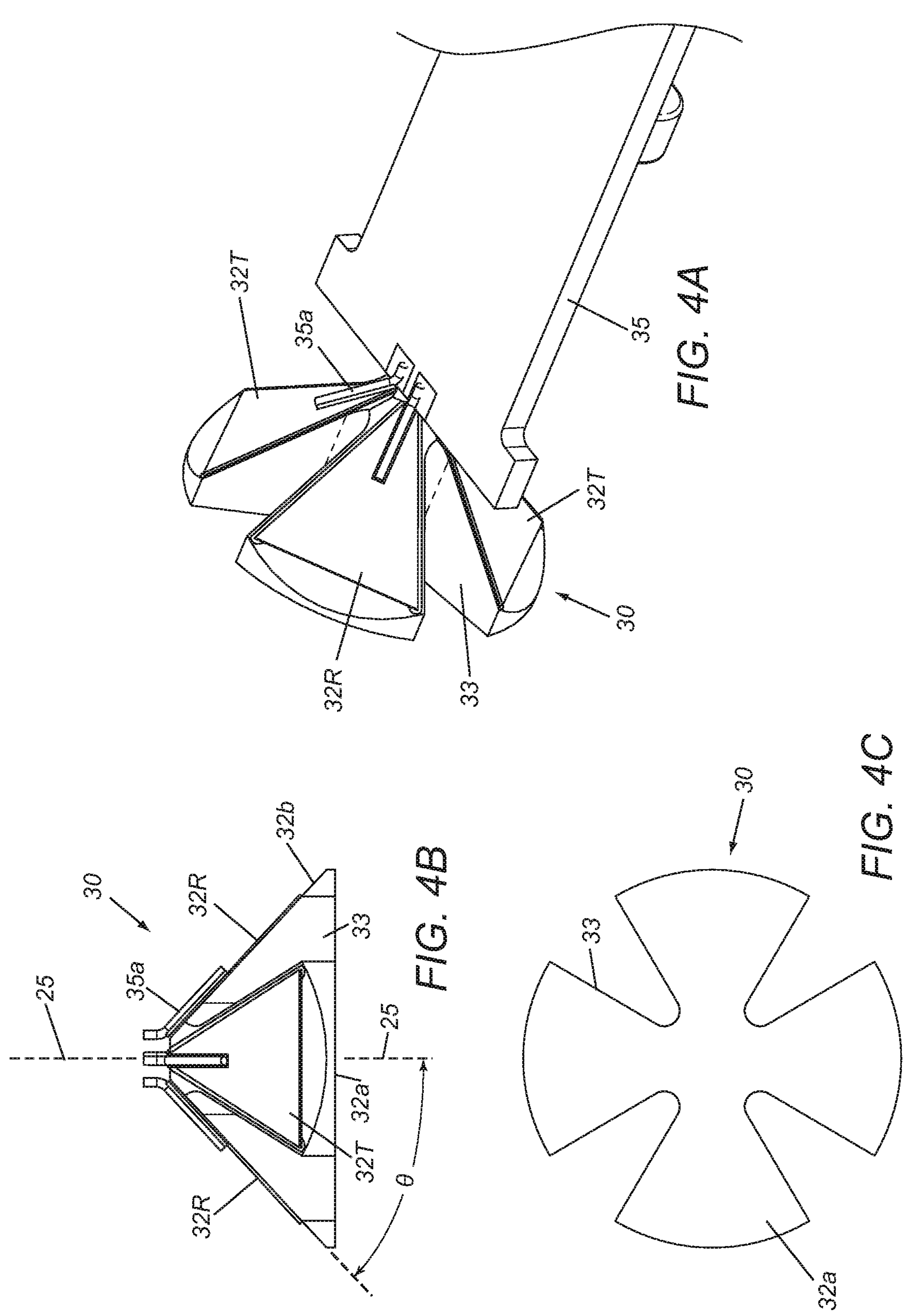
FIGS. 4A-4C are perspective, side, and bottom views of an exemplary antenna assembly that may be included in the probe of FIGS. 3A and 3B.

The probe 20 is a portable device having electromagnetic signal emitting and receiving capabilities, e.g., an elongate handheld device including a first or proximal end 22, e.g., which may be held by a user, and a second or distal end 24 intended to be placed against or adjacent tissue, e.g., a patient's skin or underlying tissue, defining longitudinal axis 25 therebetween. Generally, the probe 20 includes one or more antennas, e.g., mounted or carried on an antenna assembly 30, e.g., as shown in FIGS. 4A-4C, including one or more transmit antennas 32T and receive antennas 32R on a base 32, as described further below. In addition, the probe 20 includes a light transmitter, e.g., a plurality of light fibers 28 (shown in FIG. 3C), configured to transmit light pulses 28*a* into tissue contacted by the distal end 24, e.g., generally along the longitudinal axis 25 into breast tissue 90, as shown in FIG. 9. The light fibers 28 may be coupled to a light source (not shown), e.g., by coupling 29 (shown in FIG. 9), such that light from the light source passes through the light fibers 28 distally from the distal end 24 of the probe 20.

In an exemplary embodiment, the light source is an infrared light source, e.g., capable of delivering near infrared light between, for example, eight hundred and nine hundred fifty nanometers (800-950 nm) wavelength. Optionally, the light fibers 28 may include one or lenses, filters, and the like (not shown), if desired, for example, to focus the light transmitted by the probe 20 in a desired manner, e.g., in a relatively narrow beam extending substantially parallel to the longitudinal axis 25, in a wider angle beam, and the like. Alternatively, one or more light sources, e.g., IR LEDs, may be provided on the distal end 24 instead of light fibers 28 to deliver the light pulses 28*a*.

The probe 20 may include a processor within the probe housing 21 and/or display unit 38 including one or more circuits, signal generators, gates, and the like (not shown) needed to generate signals for transmission by the transmit antenna(s) 32T and/or to process signals received from the receive antenna(s) 32R. The components of the processor may include discrete components, solid state devices, programmable devices, software components, and the like, as desired.

FIG. 2 is a block diagram showing exemplary components of a controller of the probe 20 (although, alternatively, some of the components may be located within the controller/display unit 38 of FIG. 1). In the example shown, the probe 20 may include a signal generator 20*a*, an amplifier 20*b*, an analog-to-digital (A/D) converter 20*c*, and a digital signal processor (DSP) 20*d*. The signal generator 20*a*, e.g., a reference oscillator, produces an oscillating signal, such as a square wave signal, a triangular wave signal, or a sinusoidal signal.

For example, the probe 20 may include an impulse generator, e.g., a pulse generator and/or pseudo noise generator (not shown), coupled to the transmit antenna to generate transmit signals, and an impulse receiver for receiving signals detected by the receive antenna. The probe 20 may include a micro-controller and a range gate control that alternately activate the impulse generator and impulse receiver to transmit electromagnetic pulses, waves, or other signals via the transmit antenna, and then receive any reflected electromagnetic signals via the receive antenna, e.g., similar to other embodiments herein. Exemplary signals that may be used include microwave, radio waves, such as micro-impulse radar signals, e.g., in the ultralow bandwidth region.

In the example shown in FIG. 2, a square wave signal may be sent from the signal generator 20*a* to the transmit antenna(s) 32T of the antenna assembly 30 of the probe 20. When the square wave signal passes through the transmit antenna(s) 32T, the transmit antenna(s) 32T may act as a band pass filter ("BPF") and convert the square wave signal to a series of pulses or other transmit signals 34T. As such, the transmit signals 34T (shown in FIG. 9) transmitted by the probe 20 may include a series of pulses. Alternatively, the probe 20 may be configured to transmit continuous wave signals, e.g., similar to embodiments described in the publications incorporated by reference herein.

The transmit signals 34T may be transmitted into the tissue and reflected from the marker 40 (as shown in FIG. 9), as represented by the receive signals 34R. Once the transmit signals 34T are reflected from the marker 40, the reflected signals (i.e., the receive signals 34R) include a series of attenuated pulses (shown in FIG. 2).

The receive antenna(s) 32R of the antenna assembly 30 of the probe 20 may receive the receive signals 34R (shown in FIG. 6), e.g., a series of attenuated pulses, which may be inputted into amplifier 20*b* in order to amplify the gain of the pulses. The output of the amplifier 20*b* may be inputted into an A/D converter 20*c* in order to convert the amplified analog signal into a digital signal. The digital signals output from the A/D converter 20*c* may be inputted into a DSP 20*d* for further processing. The DSP 20*d* may perform a number of processing functions including, but not limited to, calculating a difference in time from the time the transmit signals 34T were sent to the time the receive signals 34R were received, determining the distance from the distal end 24 of the probe 20 to the marker 40, determining the location of the marker 40 in relation to the distal end 24 of the probe 20, measuring the amplitude of the receive signals 34R, and/or determining the direction the marker 40 in relation to the distal end 24 of the probe 20, e.g., as described in the publications incorporated by reference herein.

The probe 20 may be coupled to a display 38*a* of the display unit 38, e.g., by cables 36, for displaying information to a user of the probe 20, e.g., spatial or image data obtained via the antennas 32R and/or other output from the DSP 20*d*. Optionally, the probe 20 may include other features or components, such as one or more user interfaces, memory, transmitters, receivers, connectors, cables, power sources, and the like (not shown). For example, the probe 20 may include one or more batteries or other internal power sources for operating the components of the probe 20. Alternatively, the probe 20 may include a cable, such as one of the cables 36, that may be coupled to an external power source, e.g., standard AC power, for operating the components of the probe 20.

As shown in FIGS. 1 and 9, the internal components of the probe 20, e.g., components shown in FIGS. 3A-4C, may be provided in an outer housing or casing 21 such that the probe 20 is self-contained. For example, the casing 21 may be relatively small and portable, e.g., such that the entire probe 20 may be held in a user's hand. Optionally, a portion of the probe 20 may be disposable, e.g., a portion adjacent the distal end 24, or a disposable cover, sleeve, and the like (not shown) may be provided if desired, such that at least a proximal portion of the probe 20 may be reusable. Alternatively, the entire probe 20 may be a disposable, single-use device while the display unit 38 may be used during multiple procedures by connecting a new probe 20 to the display unit 38, which may remain out of the surgical field yet remain accessible and/or visible, as desired. Additional information on construction and/or operation of the probe 20 may be found in the publications incorporated by reference elsewhere herein.

Turning to FIGS. 3A-3C, exemplary internal components of the probe 20 are shown (after removing the outer housing 21), e.g., including an internal sleeve or housing 26 carrying the antenna assembly 30, and, optionally, shielding 37, on or within its distal end 26*b*.

With additional reference to FIGS. 4A-4C, the antenna assembly 30 includes a base 32 including a substantially planar distal surface 32*a*, e.g., extending perpendicular to axis 25, and a plurality of proximal planar surfaces 32*b* including antenna elements 32T, 32R. The distal surface 32*a* may be located at a distal-most location of the distal end 24 of the probe 20, e.g., such that the distal surface 32*a* may be placed directly against tissue (e.g., covered with a thin membrane or cover to prevent fluids from entering the probe and/or other contamination). The base 32 may be formed from ceramic and/or other nonconductive material, e.g., having desired dielectric properties. For example, the base 32 may be formed from material having a dielectric constant (permittivity) similar to the tissue type the probe is intended to be used with, e.g., a dielectric constant similar to human breast tissue, skin, muscle, bone, fat or other tissue. Accordingly, the base 32 material may comprise a dielectric constant ranging from about 1 to about 100, e.g., about 1-14 for embodiments intended for use with fat, about 5-8 for embodiments intended for use with breast tissue, about 60-70 for embodiments intended for use with muscle, about 70-80 for embodiments intended for use with skin, and about 6-25 for embodiments intended for use with bone.

In the embodiment shown in FIGS. 4A and 4B, the base 32 includes four planar proximal surfaces 32*b* such that a plane of each proximal surface 32*b* defines an acute angle 0 with the axis 25, e.g., between about thirty and sixty degrees) (30-60°, with the proximal surfaces 32*b* offset ninety degrees from one another around the axis 25 such that the proximal surfaces 32*b* define a generally pyramid shape. Alternatively, the proximal surfaces may have nonplanar shapes, e.g., convex or concave surfaces (not shown) that taper from the distal surface to a proximal end of the base (not shown).

In this configuration, the antenna elements may include a pair of transmit antennas 32T and a pair receive antennas 32R arranged in bowtie configurations on the proximal surfaces 32*b* of the base 32, e.g., with the transmit antennas 32T offset ninety degrees (90°) from the receive antennas 32R to define a Maltese cross antenna. Each of the antenna elements 32T, 32R may be formed separately and then attached to the corresponding proximal surfaces 32*b* or may be deposited directly onto the proximal surfaces 32*b*. In an exemplary embodiment, the antenna elements 32T, 32R may be formed from silver film or other material deposited onto the proximal surfaces 32*b* of the base 32.

Circuitry 35, e.g., a printed circuit board, flex circuit, and the like, may be coupled to the antennas 32T, 32R, e.g., including a PCB on which are provided one or more transformers and/or connectors (not shown) coupled to the respective antenna elements 32T, 32R by appropriate leads 35*a*. As shown in FIGS. 3A and 3B, coaxial cables or other leads 35*b* may be coupled to connectors on the PCB to allow the antenna elements 32T, 32R to be coupled to other components of the system, e.g., to cause the antenna elements 32T to transmit signals and/or to communicate received signals to other components of the system 10, similar to other embodiments described herein.

As shown in FIGS. 4A-4C, the base 32 also includes a plurality of radial slots 33, e.g., a slot 33 between adjacent planar surfaces 32*b*. The slots 33 may extend axially from the distal surface 32*a* to the proximal surfaces 32*b* to substantially isolate the antenna elements 32T, 32R from one another by air within the slots 33, which may increase sensitivity, reduce crosstalk and/or other noise, and the like. Alternatively, the slots 33 may be filled with other insulating material, e.g., foam and the like (not shown), which may have a desired relatively low dielectric constant to substantially isolate the antenna elements 32T, 32R from one another. In addition, as shown in FIG. 3C, light fibers 28 may be positioned within one or more of the slots 33, e.g., to deliver light pulses beyond the distal surface 32*a* of the base 32, as described elsewhere herein.

Optionally, as shown in FIGS. 3A and 3B, the base 32 may be mounted within shielding 37, which may in turn, be coupled to the distal end 26 *b* of the inner housing 26 (and/or the distal end 24 of the outer housing 21), e.g., by one or more of bonding with adhesive, sonic welding, fusing, cooperating connectors (not shown), and the like. For example, the shielding 37 may include an annular inner insulation layer 37A, e.g., formed from a collar of nylon or other polymeric material, surrounded by a relatively thin outer shield 37B, e.g., formed from copper or other material, to provide a Faraday shield. In an exemplary embodiment, a layer of copper tape may be wrapped around the inner shield with the ends secured together. Alternatively, the outer shield may be a sleeve of shielding material into which the inner shield may be inserted and attached, e.g., by bonding with adhesive, interference fit, and the like.

The shielding 37 may have a length (i.e., along the axis 25) substantially longer than a thickness of the base 32 (i.e., the distance along the axis 25 from the distal surface 32 *a* to a proximal end of the base 32). For example, the inner shield may include an annular recess (not shown) into which the base 32 may be inserted and attached, e.g., by interference fit, bonding with adhesive, and the like. The distal surface 32 *a* of the base 32 may be substantially flush with the distal end of the shielding 37 such that the distal surface 32 *a* may contact tissue during use, as described elsewhere herein. Optionally, a Mylar® film or other relatively thin layer of material (not shown) may be provided over the distal surface 32 *a* of the base 32 and/or the shielding 37, e.g., to prevent fluids or other material entering the tip, reduce contamination, and/or otherwise protect the tip of the probe 20.

With continued reference to FIGS. 4A and 4B, the proximal surfaces 32*b* of the base 32 may be exposed to a region of air within the shielding 37. Because of the low dielectric constant of air (e.g., close to one (1)), the air provides a dielectric or impedance mismatch with the material of the base such the transmission from the transmit antenna 32T is focused distally, i.e., towards the tissue contacted by the base 32. With the material of the base 32 chosen to substantially match the dielectric constant of tissue, the depth of transmission into the tissue may be enhanced. The air behind the base 32 may minimize lost energy that would otherwise be emitted by the transmit antenna 32T away from the tissue. The air behind the base 32 within the shielding 37 may also minimize crosstalk, noise and/or may otherwise enhance operation of the probe 20.

In addition, given the angled orientation of the antenna elements 32T, 32R on the proximal surfaces 32*b*, signals transmitted by the antenna elements 32T and/or received from the antenna elements 32R may be focused more narrowly along the longitudinal axis 25, e.g., to enhance directionality of the probe 20. In addition, providing antenna elements 32T, 32R extending at an angle relative to the axis 25 may reduce an outer profile of the base 32 (and consequently, an outer diameter or other cross-section of the distal end 24 of the probe 20) for a given size antenna element, e.g., as compared to the same size antenna elements being provided on a flat proximal surface of a base (not shown), such as that disclosed in the publications incorporated by reference herein, which may allow an outer profile of the probe 20 to be reduced without reducing power and/or sensitivity of the probe 20.

The probe 20 and system 10 may be used during a medical procedure, for example, in a breast biopsy or lumpectomy procedure, e.g., to facilitate localization of a lesion or other target tissue region using one or more markers. For example, turning to FIGS. 5A and 5B, an exemplary embodiment of a passive marker or tag 40 is shown that may be implanted within a patient's body, such as within a breast 90, e.g., as shown in FIG. 9. Generally, the marker 40 includes an electronics package 42 coupled to a pair of wires or antennas 44. In an exemplary embodiment, each wire 44 may be an elongate member, e.g., a solid or hollow structure having a diameter or other maximum cross-section between about half and two millimeters (0.5-2 mm) and a length between about one and ten millimeters (1.0-10 mm). The wires 44 may be formed from elastic or superelastic material and/or from shape memory material, e.g., stainless steel, Nitinol, and the like, such that the wires 44 are biased to a predetermined shape when deployed within tissue, but may be elastically deformed, e.g., to facilitate delivery, as explained elsewhere herein. Alternatively, the wires 44 may be substantially rigid such that the marker 40 remains in a substantially fixed, e.g., linear or curved, shape. As described elsewhere herein, the wires 44 may act as antennas and/or otherwise cooperate with electrical components within the electronics package 42.

Figures 5A, 5B:
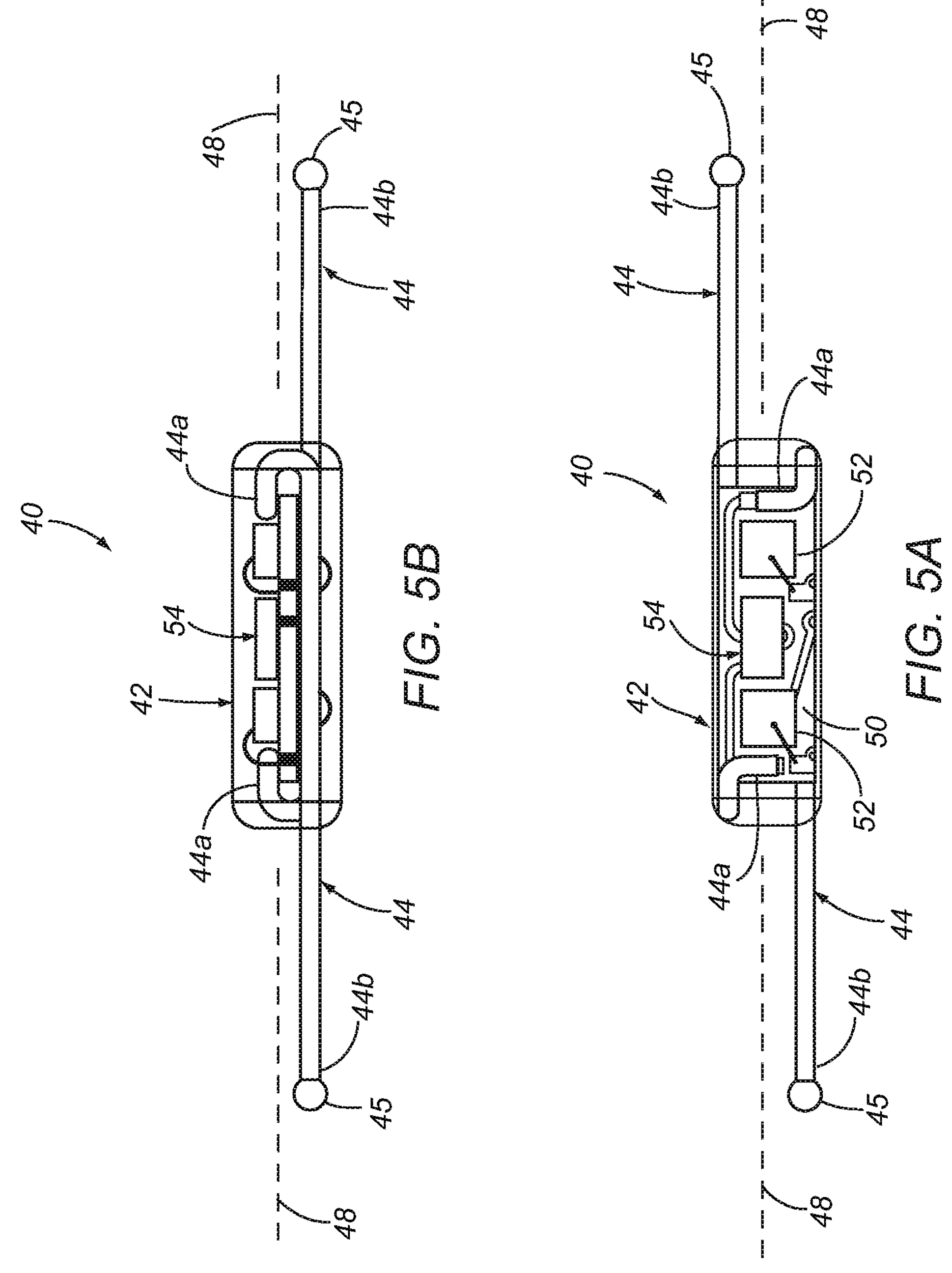
FIGS. 5A and 5B are top and side end views, respectively, of an exemplary embodiment of a marker for implantation within a patient's body.

As shown in FIGS. 5A and 5B, the wires 44 may be biased to assume a substantially linear configuration, e.g., such that the wires 44 extend substantially parallel to a longitudinal axis 48 of the marker 40. Optionally, one or both wires 44 may be offset from the longitudinal axis 48, which may enhance loading the marker 40 within a delivery device (not shown), as described elsewhere herein. Optionally, the wires 44 may carry one or more beads or other elements (not shown), e.g., similar to embodiments described in the publications incorporated by reference herein.

As shown, each wire 44 may include a first end 44*a* coupled to a printed circuit board (PCB) or other circuit 50 within the package 42 and a second free end 44*b* terminating in an enlarged and/or rounded tip 45. Optionally, the first ends 44*a* may include one or more bends, e.g., to facilitate coupling the first ends 44*a* to the circuit 50 and/or such that the wires 44 extend tangentially from opposite sides of the package 42. Alternatively, the wires 44 may be biased to assume a curvilinear or other configuration, e.g., a helical, serpentine or other curved shape, around the longitudinal axis 48. For example, the wires 44 may be formed from elastic or superelastic material that is shape set such that the wires 44 are biased to the helical configuration shown, yet may be resiliently straightened to a substantially linear configuration, e.g., to facilitate loading the marker 40 into a delivery device and/or otherwise introducing the marker 40 into a patient's body, e.g., as described in the applications incorporated by reference herein.

With additional reference to FIG. 6, the marker 40 may include one or more circuits or other electrical components 50 encased or embedded in the electronics package 42 and configured to modulate incident signals from the probe 20. In an exemplary embodiment, a semiconductor chip, print circuit board (PCB), and/or other circuit 50 may be carried in the package 42 that includes a voltage or power source or other power or energy converter 52, a switch 54 that may be opened and closed when the energy converter 52 generate electrical energy, and an Electro Static Discharge (ESD) protection device 58.

In an exemplary embodiment, the energy converter 52 includes a plurality of photosensitive diodes capable of transforming incident light (e.g., infrared light) striking them into electrical energy (e.g., a predetermined minimum voltage). As shown, multiple pairs of diodes 52 may be connected in series, which may be arranged orthogonally to one another spatially within the package 42. For example, given that photosensitive diodes are directional, at least two pairs of diodes 52 may be mounted within the package 42 offset one hundred eighty degrees (180° or otherwise relative to one another, e.g., such that at least one pair of diodes 52 may receive light from a light transmitter of the probe 20 regardless of the orientation of the marker 40 relative to the probe 20 after implantation. The package 42 may be at least partially transparent or the diodes 52 may be exposed such that light directed towards the package 42 may be received by the diodes 52. In addition or alternatively, the package 42 and/or the diodes 52 may include one or more coatings and/or filters, e.g., as disclosed in the applications incorporated by reference herein.

In the embodiment shown in FIG. 6, the switch 54 may be a field effect transistor (FET), e.g., a junction field effect transistor (JFET), with one end of the diodes 52 coupled to the gate (G) and the other coupled to the source(S), with a resistor 56 coupled between the gate (G) and the source(S), e.g., to discharge the diodes 52 when there is no IR light. In an exemplary embodiment, the switch 54 may include an enhancement mode pseudomorphic high electron mobility transistor (E-pHEMT), such as a VMMK-1225 manufactured by Avago Technologies US Inc., and the resistor 56 may be a three mega-Ohm (3M) resistor. In an alternative embodiment, the switch 54 may be a Schottky diode coupled to the diodes 52 (or other voltage source), e.g., with opposite ends of the diode coupled to the wires 44**.

Also as shown, the source(S) of the switch 54 may be electrically coupled to one of the wires 44 and the drain (D) may be coupled to the other wire 44, e.g., such that the wires 44 provide an antenna for the marker 40. For example, the components of the circuit 50 may be mounted within the package 52 such that the components are electrically isolated from one another other than as coupled in the schematic of FIG. 6. The wires 44 may be bonded or otherwise attached to the package 52 such that ends of the wires 44 are electrically coupled to the switch 54 as shown.

Each diode 52 may be capable of generating sufficient voltage (e.g., about a half Volt (0.5 V)) when exposed to light to open and close the switch 54 when there is little or no load (i.e., current draw). Since the circuit 50 is intended to be merely modulate signals from the probe 20, little or no current is needed, and so the power required from the diodes 52 (and consequently from the probe 20) may be minimal, thereby reducing power demands of the marker 40 and probe 20.

With additional reference to FIGS. 7A and 7B, light intermittently striking the diodes 52 may generate a voltage across the gate (G) and source(S) to provide a control signal that may open and close the switch 54. For example, FIG. 7A shows the switch 54 in the open configuration when infrared light is absent, while FIG. 7B shows the switch 54 in the closed configuration when infrared light 70 strikes the diodes 52, thereby connecting both wires 44 together. Thus, the result is that the marker 40 provides a passive tag that includes what equates to a high-frequency switch in the middle of the marker 40. By being able to change the switch 54 from closed to open, the reflection properties of the antenna provided by the wires 44 may be changed significantly. For example, the switch 54 may change the polarity or otherwise modulate signals reflected from the marker 40 as the switch 54 is opened and closed.

Some of the challenges involved in detecting markers implanted within breast tissue (or elsewhere in a patient's body) include the relatively small radar cross-section (RCS) of such markers and contamination of the received reflected signal, e.g., due to (a) scattering caused by tissue inhomogeneity; (b) crosstalk between transmit and receive antennas of the probe; and (c) signal distortions due to near field effects and other factors. To deal with these complicating factors and distinguish the reflected marker signal from contaminating signals received by the probe, the switch 54 provides periodic modulation of reflective properties of the marker 40.

Specifically, the marker 40 is made to periodically change its structure between two form factors, e.g., the reflectors shown in FIGS. 7A and 7B. For example, as described further elsewhere herein, digital signal processing of the received signals using ultra-wideband (UWB) radar uses synchronous detection of the signal modulated with marker switching frequency. This significantly increases the signal-to-noise (SNR) on the marker signal because other contaminating signals remain unchanged within the modulation period. To provide a mechanism for a synchronous detector, the marker switching process is controlled in the probe 20 by illuminating breast tissue with near infrared (IR) light pulses that are received by the marker 40.

Switching of the marker reflective form-factor is controlled with the set of diodes 52 operating in photovoltaic mode. When the diodes 52 receive light from the probe 20 (represented by arrows 70 in FIG. 7B), the diodes 52 generate voltage that is applied between the gate (G) and source(S) of the switch 54, which closes and connects together the drain (D) and source(S) making both antenna wires 44 connected together, as shown in FIG. 7B. When the light is off, the switch 54 is open and the drain (D) and source(S) are electrically disconnected, as shown in FIG. 7A.

In addition, the ESD device 58 may be coupled in parallel across the switch 54, e.g., between the drain (D) and source(S), to provide protection against an electrostatic discharge event. For example, use of an E-pHEMT device as switch 54 sets restrictions on the absolute maximal voltage between the drain (D) and source(S) and, therefore, across the marker's antennas. In the exemplary embodiment of a VMMK-1225 E-pHEMT, the maximal voltage across the switch 54 may be no more than about five Volts (5 V). Modern breast surgery often involves the use of electrocutting tools, electocautery tools, and/or other tools (not shown), which can generate electrical pulses of a few kV. If such a tool gets close to the marker 40, the tool can cause a very large voltage across antenna wires 44 and destroy the switch 54.

To increase survivability of the marker 40 during operation of such tools, the ESD protection device 58 truncates voltage on the switch 58 device when the voltage approaches the maximal value. Generally, the ESD protection device 58 in the marker 40 should have low capacitance that does not shunt the antennas 44 for the frequency range of the small amplitude UWB signal coming from the signals from the probe 20. In exemplary embodiments, the ESD protection device 58 may be a transient voltage suppressor, such as a Zener diode, a low-capacitance varistor, and the like.

The system 10, e.g., including probe 20 and one or more markers 40, as shown in FIG. 1, may be used during a medical procedure, for example, in a breast biopsy or lumpectomy procedure, e.g., to facilitate localization of a lesion or other target tissue region and/or to facilitate dissection and/or removal of a specimen from a breast 90 or other body structure, e.g., as shown in FIG. 9. It should be noted that, although the system 10 is described as being particularly useful in localization of breast lesions, the system 10 may also be used in localization of other objects in other areas of the body, e.g., as described in the applications incorporated by reference herein.

Before the procedure, a target tissue region, e.g., a tumor or other lesion, may be identified using conventional methods. For example, a lesion (not shown) within a breast 90 may be identified, e.g., using mammography and/or other imaging, and a decision may be made to remove the lesion. The marker 40 may be implanted within the breast 90 within or adjacent the target lesion, e.g., using a needle or other delivery device, such as the delivery device 60 shown in FIGS. 8A and 8B.

Figure 8A:
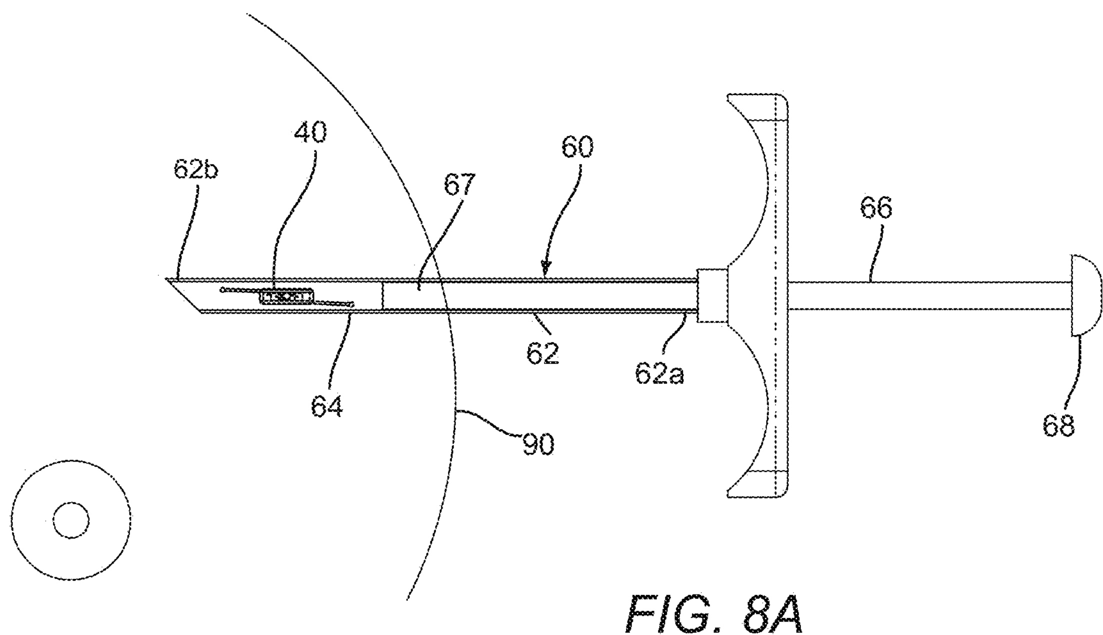
FIGS. 8A and 8B are side views of a breast, showing a delivery device being used to deliver a marker into tissue within the breast.
Figure 8B:
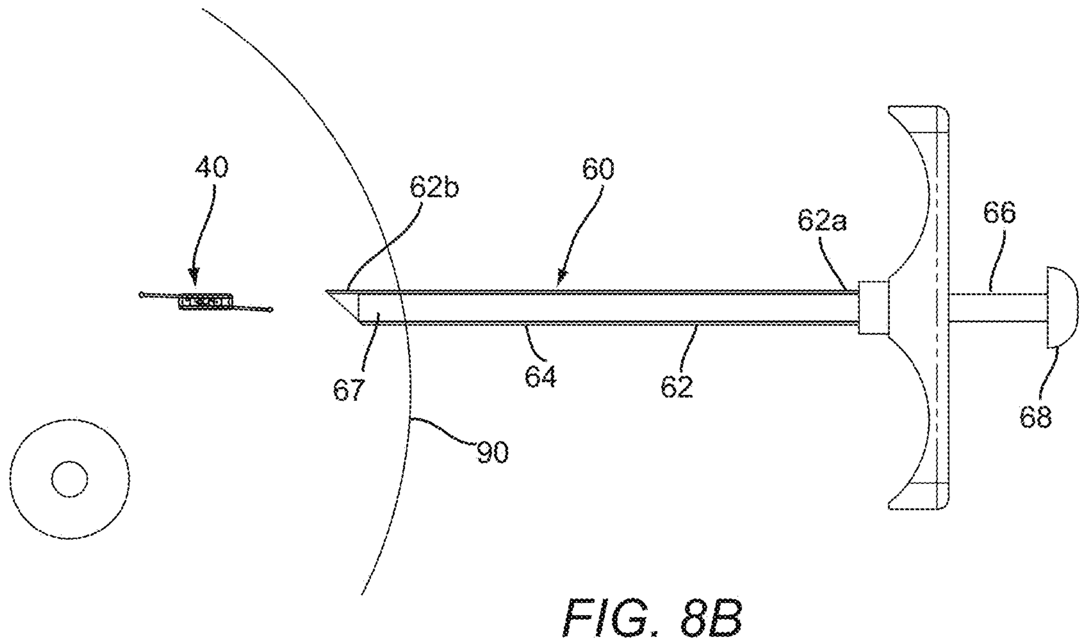

In the embodiment shown in FIGS. 8A and 8B, the delivery device 60 may include a shaft 62 including a proximal end **62*a* and a distal end 62*b* sized for introduction through tissue into a target tissue region (not shown) and carrying the marker(s) 40. The delivery device 60 may include a lumen 64 extending at least partially between the proximal and distal ends 62*a*, 62*b* of the shaft 62, and a pusher member 66 slidable within the shaft 62 for selectively delivering one or more markers 40 successively or otherwise independently from the lumen 64**.

As shown, the distal end **62*b* of the shaft 62 may be beveled, pointed, and/or otherwise sharpened such that the shaft 62 may be introduced directly through tissue. Alternatively, the delivery device 60 may be introduced through a cannula, sheath, or other tubular member (not shown) previously placed through tissue, e.g., as described in the applications incorporated by reference herein. Optionally, the distal end 62*b* may include a band or other feature, e.g., formed from radiopaque, echogenic, or other material, which may facilitate monitoring the distal end 62*b*** during introduction, e.g., using fluoroscopy, ultrasound, electromagnetic signals, and the like.

As shown, the pusher member 66 includes a piston or other element (not shown) disposed within the lumen 64 adjacent the marker(s) 40 and a plunger or other actuator 68 coupled to the piston to push the marker(s) 40 from the lumen 64. For example, as shown in FIG. 8A, the distal end **62*a* of the shaft 62 (carrying the marker 40 therein) may be inserted into the breast 90 (or other tissue) and advanced or otherwise positioned to place the marker 40 at a target location, e.g., within a cancerous lesion (not shown). Optionally, external imaging may be used to confirm the location of the marker 40 relative to the lesion. Once at the target location, the shaft 62 may be withdrawn relative to the pusher member 66, thereby deploying the marker 40, as shown in FIG. 8B. Optionally, the delivery device 60 may carry multiple markers (not shown), and the shaft 62** may be repositioned one or more times to deploy additional markers.

Alternatively, if desired, the pusher member 66 may be advanced to deploy the marker(s) 40 successively from the lumen 64, rather than retracting the shaft 62. In another alternative, a trigger device or other automated actuator (not shown) may be provided on the proximal end **62*a* of the shaft 62, which may retract the shaft 62 sufficiently with each activation, e.g., to delivery an individual marker 40 from the distal end 62*b***, e.g., as described in the applications incorporated by reference herein.

Once the marker(s) 40 is implanted, as shown in FIG. 9, the probe 20 may be placed against a patient's skin, e.g., against the breast 90. Signals from the antenna(s) 32T of the probe 20 may be delivered along with pulsed light from the light source to cause the switch 54 to open and close as the marker 40 receives and reflects the signals back to the probe 20. If there is substantial clutter, crosstalk, or other noise being received by the probe 20, e.g., due to the probe antennas, tissue or other structures within the patient's body near the marker 40, and the like, the reflected signals from the two states (switch 54 open and closed) may be subtracted from one another, substantially eliminated the other noise, and allowing the probe 20 to identify and/or locate the marker 40. Thus, the probe 20 may use the modulated reflected signals to increase the signal-to-noise ratio of the signals.

The display **38*a* may display information to the user to facilitate locating the marker 40 within the breast 90. For example, the display 38*a* may simply be a readout providing distance, angle, orientation, and/or other data based on predetermined criteria, e.g., based on the relative distance from the marker 40 to the probe 20. The distance information may be displayed as a numerical value representing the distance in units of length, such as in inches (in.) or centimeters (cm). In addition or alternatively, a speaker 38*b* on the display unit 38 may produce an audible indication of distance, e.g., spaced-pulses that increase in speed as the probe 20 is closer to the marker 40. In another alternative, the display 38*a* may present a graphical image (e.g., a two-dimensional or three-dimensional image) depicting the marker 40, the probe 20, the distance from the probe 20 to the marker 40**, and/or a physiological picture of the body part containing the marker (e.g., the breast).

For example, as shown in FIG. 9, the distal end 24 of the probe 20 may be placed adjacent or in contact with the patient's skin, e.g., generally above the lesion, and/or otherwise aimed generally towards the lesion and marker 40, and activated. The transmit antenna (not shown) of the probe 20 may emit electromagnetic signals 34T that travel through the tissue and are reflected off of the marker 40. Return signals 34R may be reflected back to the receive antenna (not shown) in the probe 20, which may then determine a spatial relationship between the marker 40 and the distal end 24 of the probe 20, e.g., a distance and/or orientation angle, to facilitate determining a proper direction of dissection for the surgeon.

In addition, substantially simultaneously, the probe 20 may transmit light pulses **38*a*, which may be received by the diodes 52 of the marker 40 (not shown, see, e.g., FIGS. 7A and 7B). The diodes 52 may alternately generate a voltage, causing the switch 54 to open and close. This causes the marker 40 to change the phase of the signals reflected back to the probe 20, which may process the signals, e.g., by subtraction, to identify and/or locate the marker 40**, and consequently the target lesion.

Tissue may then be dissected, e.g., by creating an incision in the patient's skin and dissecting intervening tissue to a desired depth, e.g., corresponding to a target margin around the lesion is reached. A tissue specimen may be excised or otherwise removed using conventional lumpectomy procedures, e.g., with the marker 40 remaining within the removed specimen 1046.

It will be appreciated that elements or components shown with any embodiment herein are exemplary for the specific embodiment and may be used on or in combination with other embodiments disclosed herein.

While the present disclosure is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for localizing a marker within a body, the method comprising:

placing a distal end of a probe against tissue, the probe comprising an antenna assembly adjacent the distal end comprising:

a plurality of antenna elements; and a base comprising nonconductive material, an exterior of the base forming:

a planar distal surface placed adjacent the tissue, and a plurality of proximal surfaces extending from a peak to the planar distal surface at an acute angle relative to a longitudinal axis of the probe, such that the base defines a pyramidal shape, wherein the antenna elements are positioned on each proximal surface, such that the proximal surfaces of the base provide a support for the antenna elements at the acute angle;

transmitting, by one or more transmit antenna elements on one or more of the proximal surfaces, transmit signals into the body;

receiving, by one or more receive antenna elements on one or more of the proximal surfaces, receive signals that are reflected from the marker; and identifying or localizing the marker based at least in part on the receive signals.

2. The method of claim 1, wherein identifying the marker comprises providing an output proportional to a distance from the distal end to the marker.

3. The method of claim 1, wherein the base comprises four proximal surfaces spaced apart from one another, and wherein the one or more transmit antenna elements comprise a bowtie transmit antenna and the one or more receive antenna elements comprise a bowtie receive antenna offset from the bowtie transmit antenna such that the bowtie transmit antenna and the bowtie receive antenna together form a Maltese cross antenna.

4. The method of claim 3, wherein each of the proximal surfaces define a plane defining an acute angle relative to the longitudinal axis.

5. The method of claim 1, wherein the nonconductive material comprises ceramic material that provides impedance matching with the tissue.

6. The method of claim 5, wherein a region adjacent the proximal surfaces provides a dielectric or impedance mismatch with the ceramic material of the base to enhance directionality of the transmit signals distally from the probe into the body.

7. The method of claim 1, further comprising determining a distance from the distal end to the marker based at least in part on the transmit and receive signals.

8. The method of claim 1, further comprising generating, via a signal generator, an oscillating signal that is sent to the one or more transmit antenna elements, which converts the oscillating signal to a pulsed signal for transmission into the body.

9. The method of claim 1, wherein the base comprises slots between adjacent proximal surfaces to isolate the transmit and receive antenna elements from one another.

10. The method of claim 1, wherein the probe further comprises shielding surrounding the distal end to shield the transmit and receive antenna elements.

11. The method of claim 10, wherein the shielding comprises an inner insulation layer and an outer Faraday shield surrounding the inner insulation layer.

12. The method of claim 1, wherein the antenna elements are positioned on each proximal surface, such that the proximal surfaces of the base provide a support for the transmit and receive antenna elements at the acute angle.

13. The method of claim 1, further comprising displaying, on a display, a distance from the distal end to the marker.

14. A method for localizing a marker within a body, the method comprising:

placing a distal end of a probe against tissue, the probe comprising:

a plurality of antenna elements; and a base comprising nonconductive material, an exterior of the base forming:

a planar distal surface extending perpendicular to a longitudinal axis, and a plurality of proximal surfaces extending from a peak at the longitudinal axis to the planar distal surface at an acute angle relative to the longitudinal axis, such that the base defines a pyramidal shape, wherein the antenna elements are positioned on each proximal surface, such that the proximal surfaces of the base provide a support for the antenna elements at the acute angle;

controlling transmit signals that are transmitted into the body by one or more of the antenna elements; and identifying or localizing the marker based on reflected signals received from the marker received by one or more of the antenna elements.

15. The method of claim 14, wherein identifying the marker comprises providing an output proportional to a distance from the distal end to the marker.

16. The method of claim 14, wherein the base comprises four proximal surfaces spaced apart from one another, and wherein the one or more transmit antenna elements comprise a bowtie transmit antenna and the one or more receive antenna elements comprise a bowtie receive antenna offset from the bowtie transmit antenna such that the bowtie transmit antenna and the bowtie receive antenna together form a Maltese cross antenna.

17. The method of claim 14, wherein the nonconductive material comprises ceramic material that provides impedance matching with the tissue.

18. The method of claim 17, wherein a region adjacent the proximal surfaces provides a dielectric or impedance mismatch with the ceramic material of the base to enhance directionality of the transmit signals distally from the probe into the body.

* * * * *